United States Patent
Gelli et al.

(10) Patent No.: US 10,724,109 B2
(45) Date of Patent: Jul. 28, 2020

(54) COMPOSITIONS AND METHODS FOR ENHANCING RESISTANCE TO ANTHRACNOSE IN GRAIN SORGHUM

(71) Applicant: PIONEER HI-BRED INTERNATIONAL, INC., Johnston, IA (US)

(72) Inventors: Malleswari Gelli, Johnston, IA (US); David Alan Hessel, St. George, KS (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 0 days.

(21) Appl. No.: 16/099,007

(22) PCT Filed: May 2, 2017

(86) PCT No.: PCT/US2017/030500
§ 371 (c)(1),
(2) Date: Nov. 5, 2018

(87) PCT Pub. No.: WO2017/196581
PCT Pub. Date: Nov. 16, 2017

(65) Prior Publication Data
US 2019/0153546 A1    May 23, 2019

Related U.S. Application Data

(60) Provisional application No. 62/333,964, filed on May 10, 2016.

(51) Int. Cl.
| | |
|---|---|
| C12Q 1/68 | (2018.01) |
| A01H 5/10 | (2018.01) |
| C12Q 1/6895 | (2018.01) |
| C07K 14/415 | (2006.01) |
| A01H 1/04 | (2006.01) |
| C12Q 1/6806 | (2018.01) |

(52) U.S. Cl.
CPC ............ *C12Q 1/6895* (2013.01); *A01H 1/04* (2013.01); *A01H 5/10* (2013.01); *C07K 14/415* (2013.01); *C12Q 1/6806* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2012/0096599 A1    4/2012    Kovalic et al.

FOREIGN PATENT DOCUMENTS

WO    2015195762 A1    12/2015

OTHER PUBLICATIONS

Genbank Accession No. CW255776, Sorghum methylation filtered library (LibID: 104) Sorghum bicolor genomic clone 11226421, genomic survey sequence, Feb. 5, 2014 (found online Jul. 28, 2017 https://www.ncbi.nlm.nih.gov/nucgss/CW255776).
Cuevas, Hugo et al:, Inheritance and molecular mapping of anthracnose resistance genes present in sorghum line SC112-14, Mol Breeding, 2014, vol. 34, pp. 1943-1953.
Burrell, A. Millie et al: Sequencing of an Anthracnose-Resistant Sorghum Genotype and Mapping of a Major QTL Reveal Strong Candidate Genes for Anthracnose Resistance, Crop Sci, 2015, vol. 55, pp. 790-799.
Mace, E.S. et al: Integrating sorghumwhole genome sequence information with a compendiumof sorghumQTL studies reveals uneven distribution of QTL and of gene-rich regions with significant implications for crop improvement, Theor Appl Genet, 2011, vol. 123, pp. 169-191.
Permumal, R. et al: Molecular mapping of Cg1, a gene for resistance to anthracnose (Colletotrichum sublineolum) in sorghum, Euphytica, 2009, vol. 165, pp. 597-606.
International Search Report and Written Opinion, International Application No. PCT/US2017/30500 dated Sep. 23, 2017.

*Primary Examiner* — Medina A Ibrahim

(57) ABSTRACT

Compositions and methods useful in identifying and selecting sorghum plants with increased resistance to anthracnose are provided herein. The methods use molecular genetic markers within QTL located on chromosome 5 and on chromosome 8 to identify and select plants with increased resistance to anthracnose, and plants comprising the QTL alleles associated with increased resistance to anthracnose can be crossed to other sorghum plants to incorporate the increased resistance into other sorghum lines or varieties.

12 Claims, No Drawings
Specification includes a Sequence Listing.

COMPOSITIONS AND METHODS FOR ENHANCING RESISTANCE TO ANTHRACNOSE IN GRAIN SORGHUM

CROSS-REFERENCE TO RELATED APPLICATIONS

This application claims priority to International Patent Application PCT/US2017/030500 filed on May 2, 2017, which claims priority to U.S. Provisional Application No. 62/333,964, filed May 10, 2016, which is hereby incorporated herein in its entirety by reference.

FIELD

The field is in the area of plant breeding and genetics.

REFERENCE TO SEQUENCE LISTING SUBMITTED ELECTRONICALLY

The official copy of the sequence listing is submitted electronically via EFS-Web as an ASCII formatted sequence listing with a file named BB2504WOPCT_SequenceListing_ST25.txt created on Mar. 23, 2017 and having a size of 2 kilobytes and is filed concurrently with the specification. The sequence listing contained in this ASCII formatted document is part of the specification and is herein incorporated by reference in its entirety.

BACKGROUND

*Sorghum* is the world's fifth most important cereal crop, after wheat, rice, maize, and barley. Besides being an increasingly important food crop for the world population, sorghum is also an important animal feed used in many countries. Moreover, sorghum is currently the second source of grain-based ethanol in US after maize.

Anthracnose (*Colletotrichum sublineolum*) is a major fungal pathogen of grain sorghum which can lead to significant yield losses (from 20 to 80%) in susceptible genotypes, particularly in tropical and subtropical regions. All parts of the plant are affected. Crop rotation is suggested for management of anthracnose infection; however, it is not always feasible and more importantly, is not always effective. Host plant resistance is the most effective means for control.

Selection through the use of molecular markers associated with increased anthracnose resistance allows selections based solely on the genetic composition of the progeny. As a result, plant breeding can occur more rapidly, thereby generating sorghum plants with increased anthracnose resistance.

SUMMARY

Compositions and methods for identifying and/or selecting (i.e. obtaining) sorghum plants having increased resistance to anthracnose are provided herein.

In one embodiment, a method of identifying and/or selecting a sorghum plant with increased resistance to anthracnose is presented herein, the method comprising the steps of: (a) screening a population with a marker to determine if one or more sorghum plants from the population comprises a QTL allele associated with increased resistance to anthracnose, wherein the marker is located within an interval on chromosome 5 comprising and flanked by V01153-1 and V01162-1; and (b) selecting from said population at least one sorghum plant comprising the favorable allele. The method may further comprise: (c) crossing the sorghum plant to a second sorghum plant; and (d) obtaining a progeny plant that has the favorable allele The method may include selecting a sorghum plant from a breeding program if the QTL allele is detected or counter-selecting a sorghum plant if the QTL allele is not detected. In one aspect, the QTL allele associated with increased resistance to anthracnose comprises at least one of the following: a "T" at V100EF5-1, a "C" at V02017-1, and a "G" at V02249-1. In another aspect, the QTL allele associated with increased resistance to anthracnose comprises: a "T" at V100EF5-1, a "C" at V02017-1, and a "G" at V02249-1.

In another embodiment, a method of identifying and/or selecting a sorghum plant with increased resistance to anthracnose is presented herein, the method comprising the steps of: (a) screening a population with a marker to determine if one or more sorghum plants from the population comprises a QTL allele associated with increased resistance to anthracnose, wherein the marker is located within an interval on chromosome 8 comprising and flanked by V02395-1 and V02069-1; and (b) selecting from said population at least one sorghum plant comprising the favorable allele. The method may further comprise: (c) crossing the sorghum plant to a second sorghum plant; and (d) obtaining a progeny plant that has the favorable allele The method may include selecting a sorghum plant from a breeding program if the QTL allele is detected or counter-selecting a sorghum plant if the QTL allele is not detected. In one aspect, the QTL allele associated with increased resistance to anthracnose comprises at least one of the following: a "G" at V02068-1 and a "G" at V02069-1. In another aspect, the QTL allele associated with increased resistance to anthracnose comprises: a "G" at V02068-1 and a "G" at V02069-1.

In another embodiment, a method of identifying and/or selecting a sorghum plant that displays increased resistance to anthracnose is provided herein. The method comprises the steps of (a) detecting in a sorghum plant an allele of a marker locus, wherein said marker locus is located within a chromosomal interval on chromosome 5 comprising and flanked by V01153-1 and V01162-1, and said allele is associated with a haplotype comprising: a "T" at V100EF5-1, a "C" at V02017-1, and a "G" at V02249-1; (b) selecting a sorghum plant that has the allele of the marker locus that is associated with the haplotype. The method may further comprise: (c) crossing the sorghum plant to a second sorghum plant; and (d) obtaining a progeny plant that has the allele associated with the haplotype comprising a "T" at V100EF5-1, a "C" at V02017-1, and a "G" at V02249-1.

In another embodiment, a method of identifying and/or selecting a sorghum plant that displays increased resistance to anthracnose is provided herein. The method comprises the steps of (a) detecting in a sorghum plant an allele of a marker locus, wherein said marker locus is located within a chromosomal interval on chromosome 5 comprising and flanked by V01153-1 and V01162-1, and said allele is associated with a haplotype comprising: a "T" at V100EF5-1, a "C" at V02017-1, and a "G" at V02249-1; (b) selecting a sorghum plant that has the allele of the marker locus that is associated with the haplotype. The method may further comprise: (c) crossing the sorghum plant to a second sorghum plant; and (d) obtaining a progeny plant that has the allele associated with the haplotype comprising a "T" at V100EF5-1, a "C" at V02017-1, and a "G" at V02249-1.

In another embodiment, a method of identifying and/or selecting a sorghum plant that displays increased resistance to anthracnose is provided herein. The method comprises the steps of (a) detecting in a sorghum plant one or more of the following: a "T" at V100EF5-1, a "C" at V02017-1, and a "G" at V02249-1; (b) selecting a sorghum plant that has one or more of the following: a "T" at V100EF5-1, a "C" at V02017-1, and a "G" at V02249-1. The method may further comprise: (c) crossing the sorghum plant to a second sorghum plant; and (d) obtaining a progeny plant that has one or more of the following: a "T" at V100EF5-1, a "C" at V02017-1, and a "G" at V02249-1.

In another embodiment, a method of identifying and/or selecting a sorghum plant that displays increased resistance to anthracnose is provided herein. The method comprises the steps of (a) detecting in a sorghum plant an allele of a marker locus, wherein said marker locus is located within a chromosomal interval on chromosome 8 comprising and flanked by V02395-1 and V02069-1, and said allele is associated with a haplotype comprising: a "G" at V02068-1 and a "G" at V02069-1; (b) selecting a sorghum plant that has the allele of the marker locus that is associated with the haplotype. The method may further comprise: (c) crossing the sorghum plant to a second sorghum plant; and (d) obtaining a progeny plant that has the allele associated with the haplotype comprising a "G" at V02068-1 and a "G" at V02069-1.

In another embodiment, a method of identifying and/or selecting a sorghum plant that displays increased resistance to anthracnose is provided herein. The method comprises the steps of (a) detecting in a sorghum plant one or more of the following: a "G" at V02068-1 and a "G" at V02069-1; (b) selecting a sorghum plant that has one or more of the following: a "G" at V02068-1 and a "G" at V02069-1. The method may further comprise: (c) crossing the sorghum plant to a second sorghum plant; and (d) obtaining a progeny plant that has one or more of the following: a "G" at V02068-1 and a "G" at V02069-1.

Plants identified and/or selected using the methods described herein are also provided.

BRIEF DESCRIPTION OF THE SEQUENCE LISTING

The invention can be more fully understood from the following detailed description and the accompanying Sequence Listing which form a part of this application. The sequence descriptions and Sequence Listing attached hereto comply with the rules governing nucleotide and/or amino acid sequence disclosures in patent applications as set forth in 37 C.F.R. § 1.821 1.825. The Sequence Listing contains the one letter code for nucleotide sequence characters and the three letter codes for amino acids as defined in conformity with the IUPAC IUBMB standards described in Nucleic Acids Res. 13:3021 3030 (1985) and in the Biochemical J. 219 (2):345 373 (1984) which are herein incorporated by reference. The symbols and format used for nucleotide and amino acid sequence data comply with the rules set forth in 37 C.F.R. § 1.822.

SEQ ID NO:1 is the reference sequence for marker V01162-1.

SEQ ID NO:2 is the reference sequence for marker V02249-1.

SEQ ID NO:3 is the reference sequence for marker V01153-1.

SEQ ID NO:4 is the reference sequence for marker V02395-1.

SEQ ID NO:5 is the reference sequence for marker V02068-1.

SEQ ID NO:6 is the reference sequence for marker V02017-1.

SEQ ID NO:7 is the reference sequence for marker V100EF5-1.

SEQ ID NO:8 is the reference sequence for marker V02069-1.

DETAILED DESCRIPTION

The current disclosure provides for marker assisted selection of sorghum plants with increased resistance to anthracnose. Detection of loci provided herein or additional linked loci can be used in marker assisted sorghum breeding programs to produce sorghum plants with increased resistance to anthracnose.

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term "allele" refers to one of two or more different nucleotide sequences that occur at a specific locus.

"Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

An allele is "associated with" a trait when it is part of or linked to a DNA sequence or allele that affects the expression of the trait. The presence of the allele is an indicator of how the trait will be expressed.

"Anthracnose" (*Colletotrichum sublineolum*) is a major fungal pathogen of grain sorghum that infects all parts of the plant. As used herein, "increased resistance to anthracnose" refers to enhanced resistance or tolerance to the fungal pathogen. Effects may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens constitutes "enhanced" or improved fungal resistance. The embodiments of the disclosure will enhance or improve resistance to the anthracnose fungal pathogen, such that the resistance of the plant to a fungal pathogen or pathogens will increase. The term "enhance" refers to improve, increase, amplify, multiply, elevate, raise, and the like.

"Backcrossing" refers to the process whereby hybrid progeny are repeatedly crossed back to one of the parents. In a backcrossing scheme, the "donor" parent refers to the parental plant with the desired gene/genes, locus/loci, or specific phenotype to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" is a single piece of coiled DNA containing many genes that act and move as a unity during cell division and therefore can be said to be linked. It can also be referred to as a "linkage group".

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait. Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "complement" refers to a nucleotide sequence that is complementary to a given nucleotide sequence, i.e. the sequences are related by the Watson-Crick base-pairing rules.

When referring to the relationship between two genetic elements, such as a genetic element contributing to a trait of interest and a proximal marker, "coupling" phase linkage indicates the state where the "favorable" allele at the genetic element contributing to increased resistance to anthracnose is physically associated on the same chromosome strand as the "favorable" allele of the respective linked marker locus. In coupling phase, both favorable alleles are inherited together by progeny that inherit that chromosome strand.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

A plant referred to herein as "diploid" has two sets (genomes) of chromosomes.

A plant referred to herein as a "doubled haploid" is developed by doubling the haploid set of chromosomes (i.e., half the normal number of chromosomes). A doubled haploid plant has two identical sets of chromosomes, and all loci are considered homozygous.

A "favorable allele" is the allele at a particular locus that confers, or contributes to, an agronomically desirable phenotype, e.g., increased resistance to anthracnose, in a sorghum plant, and that allows the identification of plants with that agronomically desirable phenotype. A favorable allele of a marker is a marker allele that segregates with the favorable phenotype.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (their recombination frequencies). Alleles can be detected using DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify positions of markers and other loci of interest on each individual genetic map. The order of loci should not change between maps, although frequently there are small changes in marker orders due to e.g. markers detecting alternate duplicate loci in different populations, differences in statistical approaches used to order the markers, novel mutation or laboratory error.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci. Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture, or more generally, all individuals within a species or for several species. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, which can be cultured into a whole plant.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to alleles at a particular locus, or to alleles at multiple loci along a chromosomal segment.

The term "heterogeneity" is used to indicate that individuals within the group differ in genotype at one or more specific loci.

An individual is "heterozygous" if more than one allele type is present at a given locus (e.g., a diploid individual with one copy each of two different alleles).

The term "homogeneity" indicates that members of a group have the same genotype at one or more specific loci.

An individual is "homozygous" if the individual has only one type of allele at a given locus (e.g., a diploid individual has a copy of the same allele at a locus for each of two homologous chromosomes).

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

The term "inbred" refers to a line that has been bred for genetic homogeneity.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an F2). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure r2, which is calculated using the formula described by Hill, W. G. and Robertson, A, Theor. Appl. Genet. 38:226-231(1968). When r2=1, complete linkage disequilibrium exists between the two marker loci, meaning that the markers have not been separated by recombination and have the same allele frequency. The r2 value will be dependent on the population used. Values for r2 above ⅓ indicate sufficiently strong linkage disequilibrium to be useful for mapping (Ardlie et al., Nature Reviews Genetics 3:299-309 (2002)). Hence, alleles are in linkage disequilibrium when r2 values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (or MAS) is a process by which individual plants are selected based on marker genotypes.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

"Nucleotide sequence", "polynucleotide", "nucleic acid sequence", and "nucleic acid fragment" are used interchangeably and refer to a polymer of RNA or DNA that is single or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5' monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

An allele "positively" correlates with a trait when it is linked to it and when presence of the allele is an indicator that the desired trait or trait form will occur in a plant comprising the allele.

The "probability value" or "p-value" is the statistical likelihood that the particular combination of a phenotype and the presence or absence of a particular marker allele is random. Thus, the lower the probability score, the greater the likelihood that a locus and a phenotype are associated. The probability score can be affected by the proximity of the first locus (usually a marker locus) and the locus affecting the phenotype, plus the magnitude of the phenotypic effect (the change in phenotype caused by an allele substitution). In some aspects, the probability score is considered "significant" or "nonsignificant". In some embodiments, a probability score of 0.05 (p=0.05, or a 5% probability) of random assortment is considered a significant indication of association. However, an acceptable probability can be any probability of less than 50% (p=0.5). For example, a significant probability can be less than 0.25, less than 0.20, less than 0.15, less than 0.1, less than 0.05, less than 0.01, or less than 0.001.

A "production marker" or "production SNP marker" is a marker that has been developed for high-throughput purposes. Production SNP markers are developed to detect specific polymorphisms and are designed for use with a variety of chemistries and platforms. The term "progeny" refers to the offspring generated from a cross.

A "progeny plant" is a plant generated from a cross between two plants.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more polymorphic markers. A haplotype can be defined by the unique fingerprint of alleles at each marker within the specified window.

A "reference sequence" or a "consensus sequence" is a defined sequence used as a basis for sequence comparison. The reference sequence for a PHM marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

*Sorghum* is a genus of numerous species of grasses, some of which are raised for grain and many of which are used as fodder plants either cultivated or as part of pasture. *Sorghum* is in the subfamily Panicoideae and the tribe Andropogoneae. *Sorghum* is well adapted to growth in hot, arid or semi-arid areas. The many subspecies are divided into four groups: grain sorghums (such as milo), grass sorghum (for pasture and hay), sweet sorghum (used to produce sorghum syrups), and broom corn (for brooms and brushes). The name sweet sorghum is used to identify varieties of *Sorghum bicolor* that are sweet and juicy. High biomass sorghum can be used as a source of biofuels.

*Sorghum* species encompassed in this disclosure include, but are not limited to, *Sorghum almum*, *Sorghum amplum*, *Sorghum angustum*, *Sorghum arundinaceum*, *Sorghum bicolor* (primary cultivated species), *Sorghum brachypodum*, *Sorghum bulbosum*, *Sorghum burmahicum*, *Sorghum controversum*, *Sorghum drummondii*, *Sorghum ecarinatum*, *Sorghum exstans*, *Sorghum grande*, *Sorghum halepense*, *Sorghum interjectum*, *Sorghum intrans*, *Sorghum lax forum*, *Sorghum leiocladum*, *Sorghum macrospermum*, *Sorghum matarankense*, *Sorghum miliaceum*, *Sorghum nigrum*, *Sorghum nitidum*, *Sorghum plumosum*, *Sorghum propinquum*, *Sorghum purpureosericeum*, *Sorghum stipoideum*, *Sorghum timorense*, *Sorghum trichocladum*, *Sorghum versicolor*, *Sorghum virgatum*, and *Sorghum vulgare*.

The term "sorghum plant" includes whole sorghum plants, sorghum plant cells, sorghum plant protoplast, sorghum plant cell or sorghum tissue culture from which sorghum plants can be regenerated, sorghum plant calli, sorghum plant clumps and sorghum plant cells that are intact in sorghum plants or parts of sorghum plants, such as sorghum seeds, sorghum flowers, sorghum cotyledons, sorghum leaves, sorghum stems, sorghum buds, sorghum roots, sorghum root tips and the like.

A "topeross test" is a test performed by crossing each individual (e.g. a selection, inbred line, clone or progeny individual) with the same pollen parent or "tester", usually a homozygous line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances. Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

An "unfavorable allele" of a marker is a marker allele that segregates with the unfavorable plant phenotype, therefore providing the benefit of identifying plants that can be removed from a breeding program or planting.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

EMBODIMENTS

Genetic Mapping

It has been recognized for quite some time that specific genetic loci correlating with particular traits can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection).

A variety of methods well known in the art are available for detecting molecular markers or clusters of molecular markers that co-segregate with a trait of interest, such as resistance to anthracnose in sorghum. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference. Two such methods used to detect trait loci of interest are: 1) Population-based association analysis and 2) Traditional linkage analysis.

In a population-based association analysis, lines are obtained from pre-existing populations with multiple founders, e.g. elite breeding lines. Population-based association analyses rely on linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, linkage disequilibrium is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, Genetics 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

The present invention provides sorghum marker loci that demonstrate statistically significant co-segregation with resistance to anthracnose as determined by traditional linkage analysis. Detection of these loci or additional linked loci can be used in marker assisted sorghum breeding programs to produce plants with increased resistance to anthracnose.

QTL Locations

QTL on chromosomes 5 and 8 were identified as being associated with resistance to anthracnose (Example 1). The QTL on chromosome 5 is located at about 54.8-70.2 cM on a single meiosis based genetic map and can be further defined as an interval comprising and flanked by markers V01153-1 and V01162-1. The QTL on chromosome 8 is located at about 3.4-14.0 cM on a single meiosis based genetic map and can be further defined as an interval comprising and flanked by markers V02395-1 and V02069-1.

Chromosomal Intervals

Chromosomal intervals that correlate with resistance to anthracnose in sorghum are provided. A variety of methods well known in the art are available for identifying chromosomal intervals. The boundaries of such chromosomal intervals are drawn to encompass markers that will be linked to the gene(s) controlling the trait of interest. In other words, the chromosomal interval is drawn such that any marker that lies within that interval (including the terminal markers that define the boundaries of the interval) can be used as a marker for resistance to anthracnose.

Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifies the same QTL or two different QTL. Regardless, knowledge of how many QTL are in a particular interval is not necessary to make or practice the invention.

The intervals described below encompass markers that co-segregate with resistance to anthracnose in a number of populations. The clustering of markers that co-segregate with a trait within a localized region occurs in relatively small domains on the chromosomes, indicating the presence of one or more QTL in those chromosome regions. The interval was drawn to encompass markers that co-segregate with resistance to anthracnose (as well as the other related traits). The intervals are defined by the markers on their termini, where the interval encompasses markers that map within the interval as well as the markers that define the termini. An interval described by the terminal markers that define the endpoints of the interval will include the terminal markers and any marker localizing within that chromosomal domain, whether those markers are currently known or unknown. The QTL interval on chromosome 5 is defined by and includes V01153-1 and V01162-1, which are separated by approximately 15 cM on a single meiosis based genetic map. The QTL interval on chromosome 8 is defined by and includes V02395-1 and V02069-1, which are separated by approximately 10 cM on a single meiosis based genetic map.

Any marker located within these intervals can find use as a marker for resistance to anthracnose and can be used in the context of the methods presented herein to identify and/or select sorghum plants that have increased resistance to anthracnose.

The chromosome 5 interval may encompass any of the markers identified herein as being associated with resistance to anthracnose including V01162-1, V02249-1, V01153-1, V02017-1, and V100EF5-1. The chromosome 8 interval may encompass any of the markers identified herein as being associated with resistance to anthracnose including V02395-1, V02068-1, and V02069-1.

Chromosomal intervals can also be defined by markers that are linked to (show linkage disequilibrium with) a QTL marker and $r^2$ is a common measure of linkage disequilibrium in the context of association studies. For example, if the $r^2$ value of linkage disequilibrium between a chromosome 5 marker locus located at or near the QTL associated with resistance to anthracnose, for example, and another chromosome 5 marker locus in close proximity is greater than $\frac{1}{3}$ (Ardlie et al., *Nature Reviews Genetics* 3:299-309 (2002)), the loci are considered to be in linkage disequilibrium with one another.

Markers and Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with increased or decreased resistance to anthracnose, it is important to note that the marker locus is not necessarily responsible for the expression of the resistance to anthracnose phenotype. For example, it is not a requirement that the marker polynucleotide sequence be part of a gene that is responsible for the phenotype (for example, is part of the gene open reading frame). The association between a specific marker allele and a trait is due to the original "coupling" linkage phase between the marker allele and the allele in the ancestral sorghum line from which the allele originated. Eventually, with repeated recombination, crossing over events between the marker and genetic locus can change this orientation. For this reason, the favorable marker allele may change depending on the linkage phase that exists within the parent having the favorable trait that is used to create segregating populations. This does not change the fact that the marker can be used to monitor segregation of the phenotype. It only changes which marker allele is considered favorable in a given segregating population.

Methods presented herein include detecting the presence of one or more marker alleles associated with increased resistance to anthracnose in a sorghum plant and then identifying and/or selecting sorghum plants that have favorable alleles at those marker loci, or detecting the presence of a marker allele associated with decreased resistance to anthracnose and then identifying and/or counterselecting sorghum plants that have unfavorable alleles. Markers have been identified herein as being associated with resistance to anthracnose in sorghum and hence can be used to identify and select sorghum plants having increased resistance to anthracnose. Any marker within 20 cM, 15 cM, 10 cM, 9 cM, 8 cM, 7 cM, 6 cM, 5 cM, 4 cM, 3 cM, 2 cM, 1 cM, 0.9 cM, 0.8 cM, 0.7 cM, 0.6 cM, 0.5 cM, 0.4 cM, 0.3 cM, 0.2 cM, 0.1 cM or less (based on a single meiosis map) of any of the markers identified herein could also be used to identify and select sorghum plants with increased resistance to anthracnose. Any marker allele linked to and associated with the favorable alleles of the markers listed herein can be used for detection purposes in the identification and/or selection of plants with increased resistance to anthracnose.

Marker Assisted Selection

Molecular markers can be used in a variety of plant breeding applications (e.g. see Staub et al. (1996) Hortscience 31: 729-741; Tanksley (1983) Plant Molecular Biology Reporter. 1: 3-8). One of the main areas of interest is to increase the efficiency of backcrossing and introgressing genes using marker-assisted selection. A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by marker assisted selection, it is not only the gene that is introduced but also the flanking regions (Gepts. (2002). Crop Sci; 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite sorghum line. This is also sometimes referred to as "yield drag." The size of the flanking region can be decreased by additional backcrossing, although this is not always successful, as breeders do not have control over the size of the region or the recombination breakpoints (Young et al. (1998) Genetics 120:579-585). In classical breeding it is usually only by chance that recombinations are selected that contribute to a reduction in the size of the donor segment (Tanksley et al. (1989). Biotechnology 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The key components to the implementation of marker assisted selection are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germ plasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) Nucleic Acid Research 17: 6463-6471; Wang et al. (1994) Theoretical and Applied Genetics, 88:1-6). Polymorphisms arise due to variation in the number of repeat units, probably caused by slippage during DNA replication (Levinson and Gutman (1987) Mol Biol Evol 4: 203-221). The variation in repeat length may be detected by designing PCR primers to the conserved non-repetitive flanking regions (Weber and May (1989) Am J Hum Genet. 44:388-396). SSRs are highly suited to mapping and marker assisted selection as they are multi-allelic, codominant, reproducible and amenable to high throughput automation (Rafalski et al. (1996) Generating and using DNA markers in plants. In: Non-mammalian genomic analysis: a practical guide. Academic press. pp 75-135).

Various types of SSR markers can be generated, and SSR profiles can be obtained by gel electrophoresis of the amplification products. Scoring of marker genotype is based on the size of the amplified fragment. Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in sorghum (Evans et al. PLos One (2013). 8 (11): e79192).

SNP markers detect single base pair nucleotide substitutions. Of all the molecular marker types, SNPs are the most abundant, thus having the potential to provide the highest genetic map resolution (PLos One (2013). 8 (11): e79192). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in marker assisted selection. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp. 475-492; Shi (2001) Clin Chem 47, pp. 164-172; Kwok (2000) Pharmacogenomics 1, pp. 95-100; and Bhattramakki and Rafalski (2001) Discovery and application of single nucleotide polymorphism markers in plants. In: R. J. Henry, Ed, Plant Genotyping: The DNA Fingerprinting of Plants, CABI Publishing, Wallingford. A wide range of commercially available technologies utilize these and other methods to interrogate SNPs including Masscode™ (Qiagen), INVADER®. (Third Wave Technologies) and Invader PLUS®, SNAPSHOT®. (Applied Biosystems), TAQMAN®. (Applied Biosystems) and BEADARRAYS®. (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes can be more informative than single SNPs and can be more descriptive of any particular genotype. For example, a single SNP may be allele 'T' for a specific line or variety with early maturity, but the allele 'T' might also occur in the sorghum breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) Plant Molecular Biology Reporter 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the sorghum species, or even across other species that have been genetically or physically aligned with sorghum, such as maize, rice, wheat, or barley.

In general, marker assisted selection uses polymorphic markers that have been identified as having a significant likelihood of co-segregation with a phenotype, such as resistance to anthracnose in sorghum. Such markers are presumed to map near a gene or genes that regulate resistance to anthracnose in a sorghum plant, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, sorghum plants with increased resistance to anthracnose can be selected for by detecting one or more marker alleles, and in addition, progeny plants derived from those plants can also be selected. Hence, a plant containing a desired genotype in a given chromosomal region is obtained and then crossed to another plant. The progeny of such a cross would then be evaluated genotypically using one or more markers and the progeny plants with the same genotype in a given chromosomal region would then be selected as exhibiting increased resistance to anthracnose.

Markers were identified from linkage mapping analysis as being associated with resistance to anthracnose. Reference sequences for each of the markers are represented by SEQ ID NOs: 1-8. The SNPs identified herein could be used alone or in combination (i.e. a SNP haplotype) to select for plants having a favorable QTL allele (i.e. associated with increased resistance to anthracnose).

The skilled artisan would expect that there might be additional polymorphic sites at marker loci in and around the chromosome 5 and chromosome 8 markers identified herein, wherein one or more polymorphic sites is in linkage disequilibrium with an allele at one or more of the polymorphic sites in the haplotype and thus could be used in a marker assisted selection program to introgress a QTL allele of interest. Two particular alleles at different polymorphic sites are said to be in linkage disequilibrium if the presence of the allele at one of the sites tends to predict the presence of the allele at the other site on the same chromosome (Stevens, Mol. Diag. 4:309-17 (1999)).

For the chromosome 5 QTL, the marker alleles that can be used for marker associated selection of sorghum plants with increased resistance to anthracnose can be linked to and associated with any or all of the following: a "T" at V100EF5-1, a "C" at V02017-1, and a "G" at V02249-1. For the chromosome 8 QTL, the marker alleles that can be used for marker associated selection of sorghum plants with increased resistance to anthracnose can be linked to and associated with any or all of the following: a "G" at V02068-1 and a "G" at V02069-1. The markers may be linked by 20 cM, 15 cM, 10 cM, 9 cM, 8 cM, 7 cM, 6 cM, 5 cM, 4 cM, 3 cM, 2 cM, 1 cM, 0.9 cM, 0.8 cM, 0.7 cM, 0.6 cM, 0.5 cM, 0.4 cM, 0.3 cM, 0.2 cM, 0.1 cM or less (on a single meiosis based genetic map).

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Plant Compositions

*Sorghum* plants identified and/or selected by any of the methods described above are also of interest.

EXAMPLES

In the following Examples, unless otherwise stated, in which parts and percentages are by weight and degrees are Celsius. It should be understood that these Examples, while indicating embodiments of the invention, are given by way of illustration only. From the above discussion and these Examples, one skilled in the art, can make various changes and modifications of the invention to adapt it to various usages and conditions. Such modifications are also intended to fall within the scope of the appended embodiments.

Example 1

Identification of QTL Associated with Resistance to Anthracnose

A quantitative mapping approach using two different bi-parental mapping populations was used to identify genetic regions associated with resistance to anthracnose in grain sorghum. The first population ("Population 1") consisted of a set of 93 F4 lines derived from the cross of Line A×Line B and top-crossed to Line C. The other population ("Population 2") consisted of a set of 293 F4 plants derived from the cross of Line D×Line E. Both populations were evaluated using a 1-9 anthracnose score (a "1" indicating severe infection and a "9" indicating no symptoms of infection), at one location for Population 1 and another location for Population 2.

"Population 1"

Data was analyzed using the R statistical package, and phenotypic distributions were first assessed to look for any transgressive segregation or outliers. Based on the phenotypic distributions, there was a wide range of values that occurred at all possible ratings on the 1-9 scale. Mapping revealed one major peak on chromosome 5 centered at 66.65 cM on a single meiosis based genetic map. The 90% Bayesian confidence interval placed this QTL between 61.28 cM and 69.59 cM on the proprietary single meiosis based sorghum reference map. Peaks occurred at the same position when a single QTL model was deployed and when composite interval mapping (CIM) was used with 3 markers as cofactors in the analysis. Line B contributed the resistance allele. The most significant single marker in the analysis was V01162-1 (the reference sequence for which is represented by SEQ ID NO:1), which is located at 70.18 cM on a single meiosis based genetic map. Homozygotes at V01162-1 for the Line B allele had an average anthracnose score of 6.75 across the two reps, versus 4.41 if they carried two Line A alleles. The data provide good evidence that the QTL acts in an additive fashion. Moreover, the QTL was detected in both male and female populations, so resistance can be combined in hybrids.

Another chromosome 5 marker had a significant LOD value and fell within the QTL peak. This marker was V02249-1 (reference sequence is SEQ ID NO:2). Marker V02249-1 is located at 61.87 cM on a single meiosis based genetic map. To statistically validate the chromosome 5 QTL, the dataset was run through a Bayesian analysis. The same two marker associations (V01162-1 and V02249-1) on chromosome 5 were detected with similar estimates.

"Population 2"

The chromosome 5 QTL was validated in a Line D/Line E population using 293 F5 individuals and 220 SNP markers. Phenotypic evaluation took place under natural disease pressure, and two reps were utilized. Two major QTL peaks were observed, one on chromosome 5 (55.94 cM) and one on chromosome 8 (5.00 cM). Both peaks had LOD values well above the 5% permutation threshold of 4.32. Disease scores were lower on average than for the Population 1 study, and the average anthracnose scores were 4.75 for Rep 1 and 4.79 for Rep 2. The 90% confidence interval for the chromosome 5 QTL extended between 54.18 and 68.22 cM, while the 90% confidence interval for the chromosome 8 QTL was 1.65 to 9.92 cM. In this population, the chromosome 8 QTL had a larger effect than the chromosome 5 QTL. For both QTL, strong and significant marker trait associations were detected. The interval for the chromosome 5 QTL overlapped the interval detected in the Line A/Line B population.

For both QTL, the resistance allele was contributed by Line D. At the chromosome 5 QTL, the genotypic value for Line D homozygotes at marker V01153-1 (the reference sequence for which is represented by SEQ ID NO:3) was 6.269±0.20, compared to 3.647±0.20 for Line E homozygotes. Marker V01153-1 is located at 54.77 cM on a single meiosis based genetic map. At the chromosome 8 QTL, the genotypic values at marker V02395-1 (the reference sequence for which is SEQ ID NO:4) were 6.838±0.12 for Line D homozygotes and 3.922±0.14 for Line E homozygotes. V02395-1 is located at 3.35 cM on a single meiosis based genetic map. Both QTL acted additively whereby an increase of −1.3 occurred with the addition of one Line D allele.

Example 2

Empirical Validation Mapping

Two additional $F_4$ populations, generated by crossing resistant inbreds derived from Line D with a more susceptible tester inbred) were evaluated for anthracnose resistance. The parental contrasts were strong for both populations.

QTL mapping was performed on each population individually using the RStudio platform and the package Rqtl. The spatially-adjusted BLUP values and genotypic data from the 768 Illumina plex were used to calculate genotype-phenotype associations. For each population, there was a large and consistent QTL effect detected in the region of the chromosome 8 QTL identified in EXAMPLE 1. The LOD value for this QTL represented a 3 to 5 fold increase in significance over the 5% genome-wide established threshold. The peak of this QTL occurred at 15.6 cM. The QTL explained the majority of the variation in anthracnose resistance for both populations.

Across the three mapping populations (including Population 2 from EXAMPLE 1) which localized a strong QTL to the short arm of chromosome 8, two markers were able to completely distinguish the resistant from susceptible parents. These two markers were V02395-1 (3.35 cM) and V02068-1 (at 6.47 cM; the reference sequence for which is SEQ ID NO:5). The genotypic value, or phenotypic difference between the two genotypes, for these two markers was an average of 1.98, which constitutes a meaningful shift in anthracnose resistance that could be leveraged for breeding.

There was also evidence of a QTL on chromosome 5 falling in the same position as detected in EXAMPLE 1. This QTL was only detected in the two populations derived from Line D which was the original resistance source harboring the QTL allele. Although the QTL effect and significance was markedly lower than for the chromosome 8 QTL, the 5% genome-wide threshold was exceeded in both populations. For one population, the peak LOD of 4.85 occurred at 63.65 cM and the 90% confidence interval for the QTL was between 58 and 77 cM. For the second population, the peak LOD of 4.04 occurred at 57.74 cM and the 90% CI extended from 46 to 86 cM. In both populations the most significant marker association occurred for V02017-1 (the reference sequence for which is SEQ ID NO:6) and both resistant parents possess the genotype passed on from Line D.

Example 3

Validation of QTLs in Hybrids

A set of half-sib TC1 populations was evaluated for several traits including anthracnose to assess the validity of the identified QTLs in a hybrid state. One of the populations contained a resistant parent derived from Line D.

Phenotypes were spatially adjusted prior to running any analyses and outliers were removed. There was extensive variability in anthracnose resistance among the entries. The range of phenotypic values was 2.46 to 7.28 with a mean of 5.35+0.09 and a variance of 1.32. The common parent was a highly susceptible inbred with a breeding value of 3.49. Consistent signals were detected for the both the chromosome 5 and chromosome 8 QTL regions.

Example 4

Marker Assisted Selection for Resistance to Anthracnose

Markers between 58 and 64 cM on chromosome 5 are most useful for marker assisted selection of resistance to anthracnose in grain sorghum. Table 1 shows resistant versus susceptible haplotypes at three markers in the chromosome 5 interval. The reference sequence for V100EF5-1 is SEQ ID NO:7. The T/C SNP at marker V100EF5-1 is located at nucleotide position 39 in SEQ ID NO:7; the C/A SNP at marker V02017-1 is located at position 25 of SEQ ID NO:6; and the G/C SNP at marker V02249-1 is located at position 25 of SEQ ID NO:2.

TABLE 1

Haplotypes for marker assisted selection at chr. 5 QTL

| Haplotype | | Marker | | |
|---|---|---|---|---|
| | | V100EF5-1 58.3 cM | V02017-1 58.3 cM | V02249-1 61.9 cM |
| | Resistant | T | C | G |
| | Susceptible | C | C or A | G or C |

Markers between 5 and 17 cM on chromosome 8 are most useful for marker assisted selection of resistance to anthracnose in grain sorghum. Table 2 shows resistant versus susceptible haplotypes at three markers in the chromosome 8 interval. The reference sequence for marker V02069-1 is SEQ ID NO:8. The G/A SNP at marker V02068-1 is located at nucleotide position 24 of SEQ ID NO:5 and the G/C SNP at marker V02069-1 is located at nucleotide position 29 of SEQ ID NO:8.

TABLE 2

Haplotypes for marker assisted selection at chr. 8 QTL

| Haplotype | | Marker | |
|---|---|---|---|
| | | V02068-1 6.5 cM | V02069-1 14.0 cM |
| | Resistant | G | G |
| | Susceptible | A | G or C |

What is claimed is:

1. A method of identifying and/or selecting a sorghum plant having increased resistance to anthracnose, said method comprising:
   a) screening a population with a marker to determine if one or more sorghum plants from the population comprises a QTL allele associated with increased resistance to anthracnose, wherein the marker is located within an interval on chromosome 5 comprising and flanked by V01153-1 and V01162-1;
   b) selecting from said population at least one sorghum plant comprising the favorable allele;
   c) crossing the sorghum plant of (b) to a second sorghum plant: and
   d) obtaining a progeny plant that has the favorable allele.

2. The method of claim 1, wherein said QTL allele associated with increased resistance to anthracnose comprises at least one of the following: a "T" at V100EF5-1 at position 39 in SEQ ID NO:7, a "C" at V02017-1 at position 25 of SEQ ID NO:6, and a "G" at V02249-1 at position 25 of SEQ ID NO:2.

3. The method of claim 1, wherein said QTL allele associated with increased resistance to anthracnose comprises: "T" at V100EF5-1 at position 39 in SEQ ID NO:7, a "C" at V02017-1 at position 25 of SEQ ID NO:6, and a "G" at V02249-1 at position 25 of SEQ ID NO:2.

4. A method of identifying and/or selecting a sorghum plant having increased resistance to anthracnose, said method comprising:
   a) screening a population with a marker to determine if one or more sorghum plants from the population comprises a QTL allele associated with increased resistance to anthracnose, wherein the marker is located within an interval on chromosome 8 comprising and flanked by V02395-1 and V02069-1;
   b) selecting from said population at least one sorghum plant comprising the favorable allele;
   c) crossing the sorghum plant of (b) to a second sorghum plant; and
   d) obtaining a progeny plant that has the favorable allele.

5. The method of claim 4, wherein said QTL allele associated with increased resistance to anthracnose comprises at least one of the following: a "G" at V02068-1 at position 24 of SEQ ID NO:5 and a "G" at V02069-1 at position 29 of SEQ ID NO:8.

6. The method of claim 4, wherein said QTL allele associated with increased resistance to anthracnose comprises: a "G" at V02068-1 at position 24 of SEQ ID NO:5 and a "G" at V02069-1 at position 29 of SEQ ID NO:8.

7. A method of identifying and/or selecting a sorghum plant that displays increased resistance to anthracnose, said method comprising:

a) detecting in a sorghum plant an allele of a marker locus, wherein said marker locus is located within a chromosomal interval on chromosome 5 comprising and flanked by V01153-1 and V01162-1 and said allele is associated with a haplotype comprising: a "T" at V100EF5-1 at position 39 in SEQ ID NO:7, a "C" at V02017-1 at position 25 of SEQ ID NO:6, and a "G" at V02249-1 at position 25 of SEQ ID NO:2;
b) selecting a sorghum plant that has the allele of the marker locus that is associated with the haplotype;
c) crossing the sorghum plant of (b) to a second sorghum plant: and
d) obtaining a progeny plant that has the allele associated with the haplotype comprising: a "T" at V100EF5-1 at position 39 in SEQ ID NO:7, a "C" at V02017-1 at position 25 of SEQ ID NO:6, and a "G" at V02249-1 at position 25 of SEQ ID NO:2.

8. A method of identifying and/or selecting a sorghum plant that displays increased resistance to anthracnose, said method comprising:
a) detecting in a sorghum plant one or more of the following:
i) a "T" at V100EF5-1 at position 39 in SEQ ID NO:7,
ii) a "C" at V02017-1 at position 25 of SEQ ID NO:6, and
iii) a "G" at V02249-1 at position 25 of SEQ ID NO:2;
b) selecting said sorghum plant that has one or more of (i)-(iii);
c) crossing the sorghum plant of (c) with a second sorghum plant; and
d) obtaining a progeny plant that has one or more of (a)(i)-a(iii).

9. A method of identifying and/or selecting a sorghum plant that displays increased resistance to anthracnose, said method comprising:
a) detecting in a sorghum plant an allele of a marker locus, wherein said marker locus is located within a chromosomal interval on chromosome 8 comprising and flanked by V02395-1 and V02069-1 and said allele is associated with a haplotype comprising: a "G" at V02068-1 at position 24 of SEQ ID NO: 5 and a "G" at V02069-1 at position 29 of SEQ ID NO: 8;
b) selecting a sorghum plant that has the allele of the marker locus that is associated with the haplotype;
c) crossing the sorghum plant in step (b) with a second sorghum plant; and
d) obtaining a progeny plant that has the allele associated with the haplotype comprising: a "G" at V02068-1 at position 24 of SEQ ID NO: 5 and a "G" at V02069-1 at position 29 of SEQ ID NO:8.

10. A method of identifying and/or selecting a sorghum plant that displays increased resistance to anthracnose, said method comprising:

a) detecting in a sorghum plant one or more of the following:
i) a "G" at V02068-1 at position 24 of SEQ ID NO:5: and
ii) a "G" at V02069-1 at position 29 of SEQ ID NO:8;
b) selecting said sorghum plant that has one or more of (a)(i) and (a)(ii);
c) crossing the sorghum plant of step (b) with a second sorghum plant; and
d) obtaining a progeny plant that has one or more of (a)(i) and (a)(ii).

11. A method of selecting a sorghum plant that displays increased resistance to anthracnose, the method comprising:
a) obtaining a first sorghum plant that comprises within its genome: a "T" at V100EF5-1 at position 39 in SEQ ID NO:7, a "C" at V02017-1 at position 25 of SEQ ID NO:6, and a "G" at V02249-1 at position 25 of SEQ ID NO:2;
b) crossing said first sorghum plant to a second sorghum plant;
c) evaluating progeny plants for the presence of:
i) a "T" at V100EF5-1 at position 39 in SEQ ID NO:7, a "C" at V02017-1 at position 25 of SEQ ID NO:6, and a "G" at V02249-1 at position 25 of SEQ ID NO:2; or
ii) an allele of a marker locus located within a chromosomal interval defined by and including V01153-1 and V01162-1 wherein said allele is associated with a haplotype comprising: a "T" at V100EF5-1 at position 39 in SEQ ID NO:7, a "C" at V02017-1 at position 25 of SEQ ID NO:6, and a "G" at V02249-1 at position 25 of SEQ ID NO:2; and
d) selecting progeny plants that have i) or ii).

12. A method of selecting a sorghum plant that displays increased resistance to anthracnose, the method comprising:
a) obtaining a first sorghum plant that comprises within its genome: a "G" at V02068-1 at position 24 of SEP ID NO:5 and a "G" at V02069-1 at position 29 of SEP ID NO:8;
b) crossing said first sorghum plant to a second sorghum plant;
c) evaluating progeny plants for the presence of:
i) a "G" at V02068-1 at position 24 of SEQ ID NO:5 and a "G" at V02069-1 at position 29 of SEQ ID NO:8; or
ii) an allele of a marker locus located within a chromosomal interval defined by and including V02395-1 and V02069-1 wherein said allele is associated with a haplotype comprising: a "G" at V02068-1 at position 24 of SEQ ID NO:5 and a "G" at V02069-1 at position 29 of SEQ ID NO:8; and
d) selecting progeny plants that have i) or ii).

* * * * *

SEQUENCE LISTING

```
<160> NUMBER OF SEQ ID NOS: 8

<210> SEQ ID NO 1
<211> LENGTH: 46
<212> TYPE: DNA
<213> ORGANISM: Artificial
<220> FEATURE:
<223> OTHER INFORMATION: V01162-1 reference sequence

<400> SEQUENCE: 1
caacagaagc actggaatac atyagcagaa tgtcgtccta gtagca            46

<210> SEQ ID NO 2
<211> LENGTH: 45
<212> TYPE: DNA
<213> ORGANISM: Artificial
<220> FEATURE:
<223> OTHER INFORMATION: V02249-1 reference sequence

<400> SEQUENCE: 2
agccacctat cagtctagaa gaagscacac tccccgttcc ccagg             45

<210> SEQ ID NO 3
<211> LENGTH: 41
<212> TYPE: DNA
<213> ORGANISM: Artificial
<220> FEATURE:
<223> OTHER INFORMATION: V01153-1 reference sequence

<400> SEQUENCE: 3
ccacacgcac cgccaccytt tttatcgagc caatacatca a                 41

<210> SEQ ID NO 4
<211> LENGTH: 59
<212> TYPE: DNA
<213> ORGANISM: Artificial
<220> FEATURE:
<223> OTHER INFORMATION: V02395-1 reference sequence

<400> SEQUENCE: 4
cgggatcgag ttcgttgaca aactactagc sgaaataaag gtgatggttc ggggtgagc    59

<210> SEQ ID NO 5
<211> LENGTH: 45
<212> TYPE: DNA
<213> ORGANISM: Artificial
<220> FEATURE:
<223> OTHER INFORMATION: V02068-1 reference sequence
```

```
<400> SEQUENCE: 5
gcattgatcg atatgtatag ccartgcggg aagtttgagt ctgcg            45

<210> SEQ ID NO 6
<211> LENGTH: 49
<212> TYPE: DNA
<213> ORGANISM: Artificial
<220> FEATURE:
<223> OTHER INFORMATION: V02017-1 reference sequence

<400> SEQUENCE: 6
cgacctttgt caatgtttga tgtcmtgtat cgtgtaactc tgcttcgat        49

<210> SEQ ID NO 7
<211> LENGTH: 79
<212> TYPE: DNA
<213> ORGANISM: Artificial
<220> FEATURE:
<223> OTHER INFORMATION: V100EF5-1 reference sequence
<220> FEATURE:
<221> NAME/KEY: misc_feature
<222> LOCATION: (47)..(48)
<223> OTHER INFORMATION: n is a, c, g, or t

<400> SEQUENCE: 7
gctggttctt actcatcaac ttggtacagg tgctcttgyt gctccannct cacgtaatgt    60
gtttgttact cctgggacg                                                79

<210> SEQ ID NO 8
<211> LENGTH: 54
<212> TYPE: DNA
<213> ORGANISM: Artificial
<220> FEATURE:
<223> OTHER INFORMATION: V02069-1 reference sequence

<400> SEQUENCE: 8
cagtatgaca gtaatactta gctcattasa gaagatgttg atctgcacac atgg    54
```